US012685817B2

(12) United States Patent
Nakanishi et al.

(10) Patent No.: US 12,685,817 B2
(45) Date of Patent: Jul. 21, 2026

(54) LIQUID FEEDING PUMP, ADAPTER, AND LIQUID FEEDING SET

(71) Applicant: TERUMO KABUSHIKI KAISHA, Tokyo (JP)

(72) Inventors: Masaru Nakanishi, Shizuoka (JP); Hitoshi Kuboki, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 539 days.

(21) Appl. No.: 18/207,523

(22) Filed: Jun. 8, 2023

(65) Prior Publication Data

US 2023/0321346 A1 Oct. 12, 2023

Related U.S. Application Data

(63) Continuation of application No. PCT/JP2021/039149, filed on Oct. 22, 2021.

(30) Foreign Application Priority Data

Dec. 10, 2020 (JP) ................................. 2020-205380

(51) Int. Cl.
| | |
|---|---|
| *A61M 5/168* | (2006.01) |
| *A61M 39/10* | (2006.01) |
| *A61M 39/28* | (2006.01) |

(52) U.S. Cl.
CPC ........ *A61M 5/16813* (2013.01); *A61M 39/28* (2013.01); *A61M 2039/1005* (2013.01)

(58) Field of Classification Search
CPC .......... A61M 5/16813; A61M 5/16804; A61M 5/168; A61M 39/28; A61M 2205/14;
(Continued)

(56) References Cited

U.S. PATENT DOCUMENTS

| | | | | |
|---|---|---|---|---|
| 6,117,115 A | * | 9/2000 | Hill | ................... A61M 5/16813 604/67 |
| 6,261,262 B1 | | 7/2001 | Briggs et al. | |

(Continued)

FOREIGN PATENT DOCUMENTS

| | | |
|---|---|---|
| CN | 1795937 A | 7/2006 |
| CN | 102065932 A | 5/2011 |

(Continued)

OTHER PUBLICATIONS

Office Action issued in Japanese Appl. No. 2022-568092 dated May 7, 2025.
(Continued)

*Primary Examiner* — Jason E Flick
(74) *Attorney, Agent, or Firm* — Foley & Lardner LLP

(57) ABSTRACT

A liquid feeding pump for feeding liquid in a liquid feeding tube, the liquid feeding pump including: a mounting portion to which a first clip member mounted to the liquid feeding tube is mountable; an adapter detachably attachable to the mounting portion; and a detection unit configured to detect mounting of the first clip member to the mounting portion, wherein: the adapter has a shape that disables detection by the detection unit of mounting of the first clip member by the detection unit and enables detection by the detection unit of mounting of a second clip member having a shape different from a shape of the first clip member.

11 Claims, 12 Drawing Sheets

(58) Field of Classification Search
CPC ............ A61M 2039/087; A61M 39/08; A61M
2039/085; A61M 39/10; A61M
2039/1005; A61M 2039/1027; A61M
2039/1044; A61M 2039/1077; A61M
2039/1094; A61M 5/1418
See application file for complete search history.

(56) References Cited

U.S. PATENT DOCUMENTS

| | | | | |
|---|---|---|---|---|
| 6,635,033 B1 * | 10/2003 | Hill | .................. | A61M 5/16813 |
| | | | | 604/249 |
| 2014/0276536 A1 | 9/2014 | Estes | | |
| 2015/0018766 A1 * | 1/2015 | Nakanishi | ........... | A61M 39/281 |
| | | | | 604/151 |
| 2020/0086017 A1 * | 3/2020 | Jardret | ................... | A61F 13/05 |

FOREIGN PATENT DOCUMENTS

| | | | |
|---|---|---|---|
| CN | 104324432 | A | 2/2015 |
| CN | 104784771 | A | 7/2015 |
| JP | H07-507939 | A | 9/1995 |
| JP | H11-507285 | A | 6/1999 |
| JP | 3140940 | U | 4/2008 |
| JP | 2011-516164 | A | 5/2011 |
| JP | 2011-212112 | A | 10/2011 |
| JP | 2019-208575 | A | 12/2019 |
| WO | WO-2013/145060 | A1 | 10/2013 |
| WO | WO-2014/169081 | A1 | 10/2014 |

OTHER PUBLICATIONS

Office Action issued in Japanese Appl. No. 2021-561216 on Apr. 6, 2024.

International Searching Authority, "International Search Report," issued in connection with International Patent Application No. PCT/JP2021/039149, dated Jan. 11, 2022.

International Searching Authority, "Written Opinion," issued in connection with International Patent Application No. PCT/JP2021/039149, dated Jan. 11, 2022.

Office Action issued in Chinese Appl. No. 202180068574.0 dated Jan. 26, 2026.

Search Report issued in Chinese Appl. No. 202180068574.0 dated Jan. 23, 2026.

* cited by examiner

LIQUID FEEDING PUMP, ADAPTER, AND LIQUID FEEDING SET

CROSS-REFERENCE TO RELATED APPLICATIONS

This is a bypass continuation of PCT Application No. PCT/JP2021/039149, filed on Oct. 22, 2021, which claims priority to Japanese Patent Application No. 2020-205380, filed on Dec. 10, 2020. The contents of these applications are incorporated herein by reference in their entireties.

BACKGROUND

The present disclosure relates to a liquid feeding pump, an adapter, and a liquid feeding set.

For example, a liquid feeding pump disclosed in Patent Literature 1 is known as a liquid feeding pump used for infusion. The liquid feeding pump for infusion described in Japanese Patent Publication No. 2011-212112 A ("Patent Literature 1") is usually used exclusively for infusion, and is not used for feeding nutrients, in order to suppress erroneous attachment of a nutrient tube for feeding nutrients and an infusion tube for feeding an infusion solution.

SUMMARY

The fact that the liquid feeding pump described in Patent Literature 1 can be used for feeding nutrients brings about an advantage that it is not necessary to purchase a liquid feeding pump different from the liquid feeding pump for feeding the infusion solution in order to feed the nutrients.

An object of the present disclosure is to provide a liquid feeding pump capable of feeding different types of liquids while preventing erroneous attachment of tubes for feeding different types of liquids. In addition, an object of the present disclosure is to provide an adapter for enabling feeding different types of liquids to a liquid feeding pump. Furthermore, an object of the present disclosure is to provide a liquid feeding set that can be mounted to a liquid feeding pump only via the adapter described above.

According to a first aspect of the present disclosure, a liquid feeding pump for feeding liquid in a liquid feeding tube is provided. The liquid feeding pump includes: a mounting portion to which a first clip member mounted to the liquid feeding tube is mountable; an adapter detachably attachable to the mounting portion; and a detection unit that detects mounting of the first clip member to the mounting portion. The adapter has a shape that disables detection of mounting of the first clip member by the detection unit and enables detection of mounting of a second clip member having a shape different from a shape of the first clip member by the detection unit.

According to one embodiment of the liquid feeding pump of the present disclosure, the adapter defines an insertion space formed to disable insertion of the first clip member and enable insertion of the second clip member.

According to one embodiment of the liquid feeding pump of the present disclosure, the adapter includes a cover member that defines the insertion space, and a detection assisting member that is detected by the detection unit by being pressed and moved or deformed by the second clip member inserted into the insertion space.

According to one embodiment of the liquid feeding pump of the present disclosure, the first clip member is mounted to an infusion tube that feeds an infusion solution.

According to one embodiment of the liquid feeding pump of the present disclosure, the second clip member is mounted to a nutrient tube that feeds a nutrient.

According to one embodiment of the liquid feeding pump of the present disclosure, the liquid feeding pump includes a main body portion that controls feeding of the liquid, and a door portion pivotably connected to the main body portion to sandwich the liquid feeding tube together with the main body portion When the first clip member is mounted to the mounting portion in a state in which the door portion is open with respect to the main body portion, the liquid feeding tube to which the first clip member is mounted is closed.

According to one embodiment of the liquid feeding pump of the present disclosure, after the first clip member is mounted to the mounting portion, the door portion is closed with respect to the main body portion, and when the liquid feeding tube is sandwiched between the main body portion and the door portion, closing of the liquid feeding tube is released.

According to a second aspect of the present disclosure, there is provided an adapter used in a liquid feeding pump including a mounting portion to which a first clip member mounted to the liquid feeding tube is mountable; and a detection unit that detects mounting of the first clip member to the mounting portion. The adapter has a shape that disables detection of mounting of the first clip member by the detection unit and enables detection of mounting of a second clip member having a shape different from a shape of the first clip member by the detection unit, and the adapter is configured to be detachably attached to the mounting portion.

One embodiment of the adapter of the present disclosure defines an insertion space formed to disable insertion of the first clip member and enable insertion of the second clip member.

One embodiment of the liquid feeding pump of the present disclosure includes a cover member that defines the insertion space, and a detection assisting member that is detected by the detection unit by being pressed and moved or deformed by the second clip member inserted into the insertion space.

According to a third aspect of the present disclosure, a liquid feeding set used in a liquid feeding pump is provided. The liquid feeding set includes: a liquid feeding tube; and a clip member attached to the liquid feeding tube. The clip member has a shape that cannot be mounted to a mounting portion of the liquid feeding pump and can be mounted to the liquid feeding pump only via an adapter attached to the mounting portion.

According to certain embodiments of the present disclosure, it is possible to provide a liquid feeding pump capable of feeding different types of liquids while preventing erroneous attachment of tubes for feeding different types of liquids. In addition, according to the present disclosure, it is possible to provide an adapter for enabling feeding different types of liquids to a liquid feeding pump. Furthermore, according to the present disclosure, it is possible to provide a liquid feeding set that can be mounted to a liquid feeding pump only via the adapter described above.

DETAILED DESCRIPTION

Figure 1:
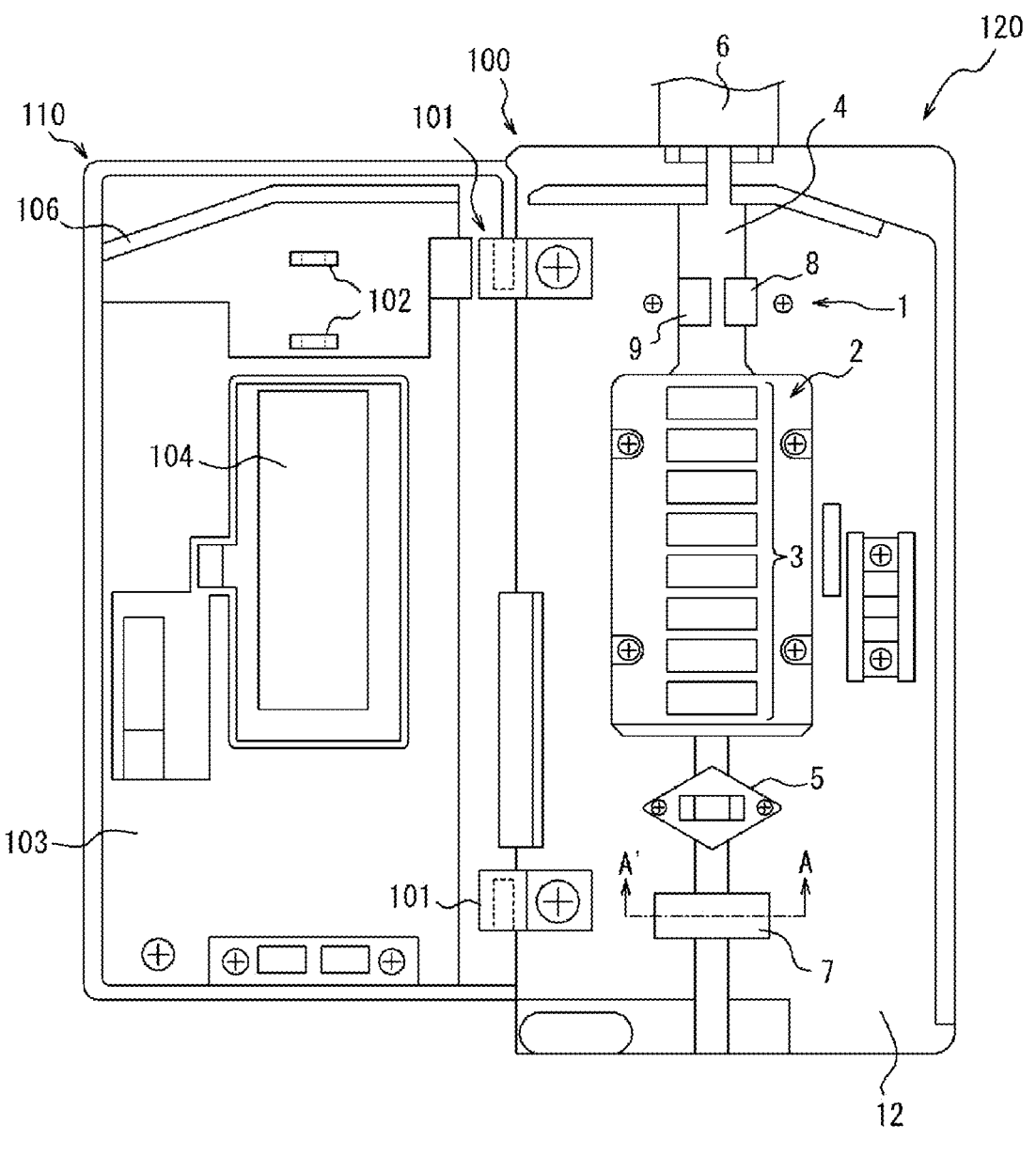
FIG. 1 illustrates a front view of a liquid feeding pump according to an embodiment of the present application.

FIG. 1 illustrates a front view of a liquid feeding pump 100 according to an embodiment of the present application. FIG. 2 illustrates a cross-sectional perspective view of the liquid feeding pump 100 taken along line AA' in FIG. 1 and a first clip member 40. FIG. 3 illustrates an adapter 10 and a second clip member 50 according to an embodiment of the present application. FIG. 4 illustrates a cross-sectional perspective view of the liquid feeding pump 100 taken along line AA' in FIG. 1 in a state in which the adapter 10 is mounted, and the second clip member 50. FIG. 5 illustrates a cross-sectional perspective view of the liquid feeding pump 100 taken along line AA' in FIG. 1 in a state in which the adapter 10 is mounted, and the first clip member 40.

The liquid feeding pump 100 includes a main body portion 120 and a door portion 110. The door portion 110 is attached to main body portion 120 to be openable and closable. In the liquid feeding pump 100 illustrated in FIG. 1, the door portion 110 is open with respect to the main body portion 120. Therefore, in FIG. 1, the front surface of the main body portion 120 and the back surface of the door portion 110 are illustrated. Hereinafter, the state in which the door portion 110 is open with respect to the main body portion 120 may be simply referred to as an "open state." In addition, the state in which the door portion 110 is closed with respect to the main body portion 120 may be simply referred to as a "closed state."

In the liquid feeding pump 100, liquid feeding tubes 55 and 46 capable of feeding an infusion solution and a nutrient as different types of liquids can be installed. The liquid feeding pump 100 can feed the liquid in the liquid feeding tubes 55 and 46 by pressing the liquid feeding tubes 55 and 46 installed. Although details will be described below, in the liquid feeding pump 100 of the present embodiment, the door portion 110 is brought into the closed state from a state in which the door portion 110 is in the open state and the liquid feeding tubes 55 and 46 are disposed at predetermined positions of the main body portion 120. Thus, the installation of the liquid feeding tubes 55 and 46 to the liquid feeding pump 100 is completed. For example, an infusion bag containing a liquid such as a predetermined medicinal solution is connected to the flow path upstream side (upper side of FIGS. 2A, 4A, 4B, and 5A) of the liquid feeding tubes 55 and 46 with respect to the portion of the liquid feeding tubes 55 and 46 installed in the liquid feeding pump 100. In addition, for example, a clamp member and an indwelling catheter are connected to the flow path downstream side (lower side of FIGS. 2A, 4A, 4B, and 5A) of the liquid feeding tubes 55 and 46 with respect to the portion of the liquid feeding tubes 55 and 46 installed in the liquid feeding pump 100. The indwelling catheter is indwelled in a state of being punctured into a vein or the like of a patient. By using the liquid feeding pump 100, the flow rate (liquid feeding speed) or the like of the liquid in the liquid feeding tubes 55 and 46 per unit time is controlled. Therefore, the amount of the liquid in the infusion bag administered to the patient per unit time or the like can be controlled by the liquid feeding pump 100.

As illustrated in FIG. 1, the main body portion 120 includes an air bubble detection sensor unit 1, a pressing portion 2, a tube position defining unit 4, a closing sensor unit 5, and a mounting portion 7.

The air bubble detection sensor unit 1 includes an ultrasonic transmission unit 8 and an ultrasonic reception unit 9. The air bubble detection sensor unit 1 detects the presence or absence of air bubbles in the liquid feeding tubes 55 and 46 in a state in which the door portion 110 is in the closed state. More specifically, the liquid feeding tubes 55 and 46 are disposed between the ultrasonic transmission unit 8 and the ultrasonic reception unit 9, and the ultrasonic transmission unit 8 transmits a predetermined signal such as an ultrasonic wave to the ultrasonic reception unit 9. In a case in which the signal intensity at which the ultrasonic signal is received is high, it is determined that no air bubble is detected, and when the signal intensity at which the ultrasonic signal is received is low, it is determined that an air bubble is detected.

The pressing portion 2 includes a plurality of fingers 3. The plurality of fingers 3 is arranged from the flow path upstream side to the flow path downstream side of the liquid feeding tubes 55 and 46. Each of the plurality of fingers 3 can reciprocate in a direction facing a receiving portion 104 of the door portion 110 described below by the driving means. The plurality of fingers 3 is driven by the drive unit described above to sequentially press and close the liquid feeding tubes 55 and 46 from the flow path upstream side toward the flow path downstream side. As a result, the liquid feeding tubes 55 and 46 can perform peristaltic movement. The pressing portion 2 of the present embodiment includes eight fingers 3, but the number of fingers is not limited to eight in the present embodiment, and may be less than eight or nine or more. In addition, in the pressing portion 2 of the present embodiment, the finger 3 forms a contact body that comes into contact with the liquid feeding tubes 55 and 46, but for example, a contact body used in a so-called "roller pump" may be formed by squeezing the liquid feeding tubes 55 and 46 using a roller that revolves around a predetermined rotation central axis and is rotatable.

The tube position defining unit 4 defines a position in a direction orthogonal to the central axis direction of the liquid feeding tubes 55 and 46 when the liquid feeding tubes 55 and 46 are mounted to the front surface of the main body portion 120.

The closing sensor unit 5 includes a permanent magnet and a pickup for analog detection of a movement amount of the permanent magnet. For example, the closing sensor unit 5 detects the closing state of the liquid feeding tubes 55 and 46 by detecting the movement amount of the permanent magnet that has moved in accordance with the internal pressure change accompanying the closing state of the liquid feeding tubes 55 and 46.

As illustrated in FIG. 1, the main body portion 120 may further include a handle 6 for the user to grip when carrying the liquid feeding pump 100.

Figure 2A:
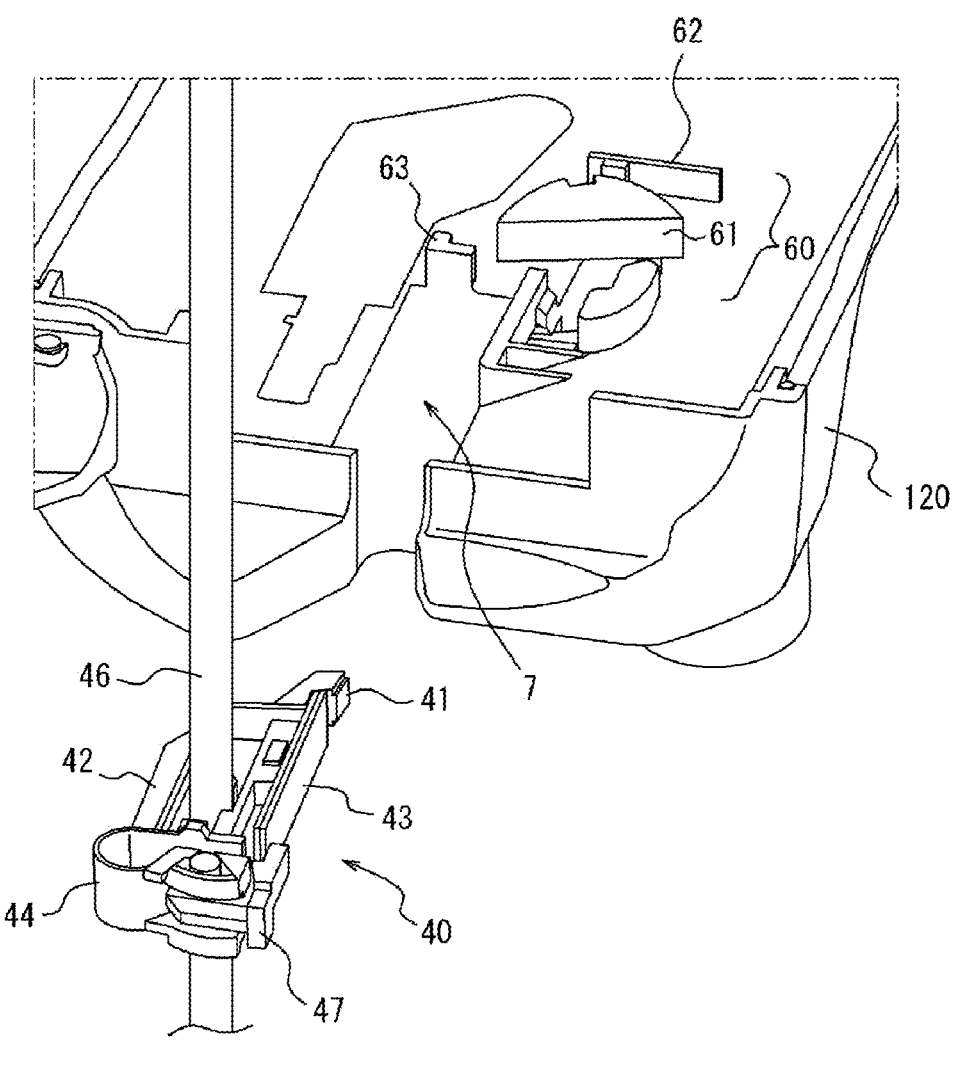
FIG. 2A illustrates a cross-sectional perspective view of the liquid feeding pump taken along line AA' in FIG. 1, and a first clip member before being mounted to a mounting portion of the liquid feeding pump illustrated in FIG. 1.
Figure 2B:
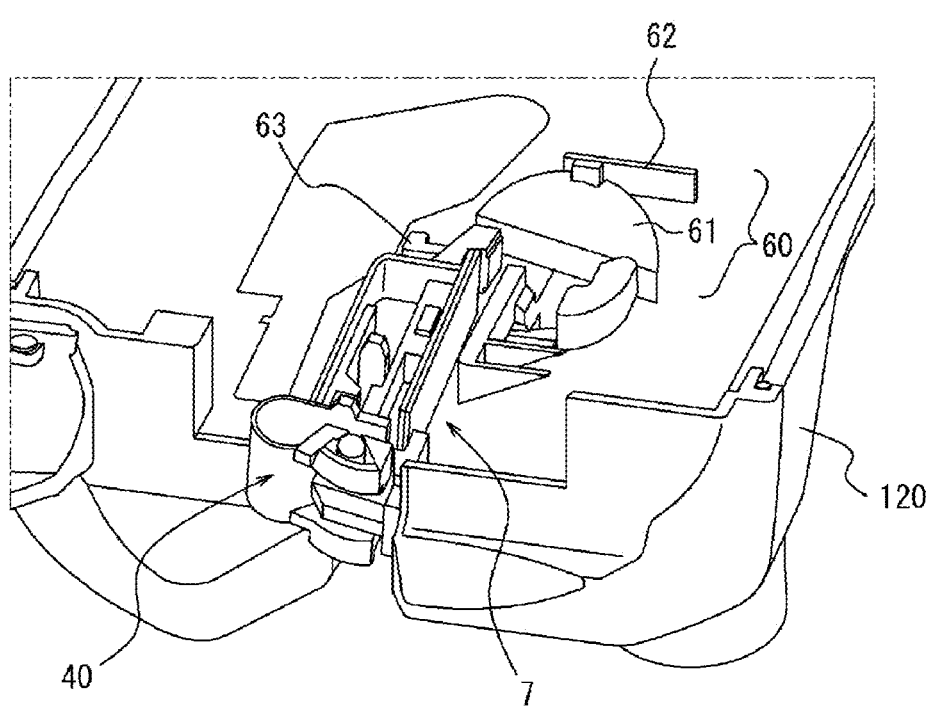
FIG. 2B illustrates a state in which the first clip member is completely mounted to the mounting portion of the liquid feeding pump from the state illustrated in FIG. 2A.
Figure 3:
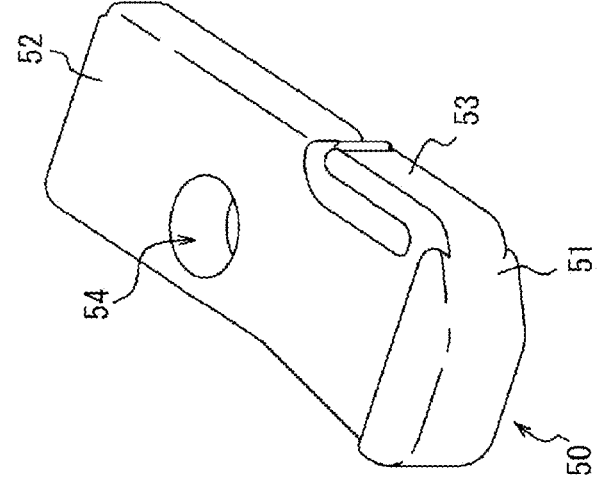
FIG. 3 illustrates an adapter according to an embodiment of the present application and a second clip member mountable to the adapter.
Figure 3:
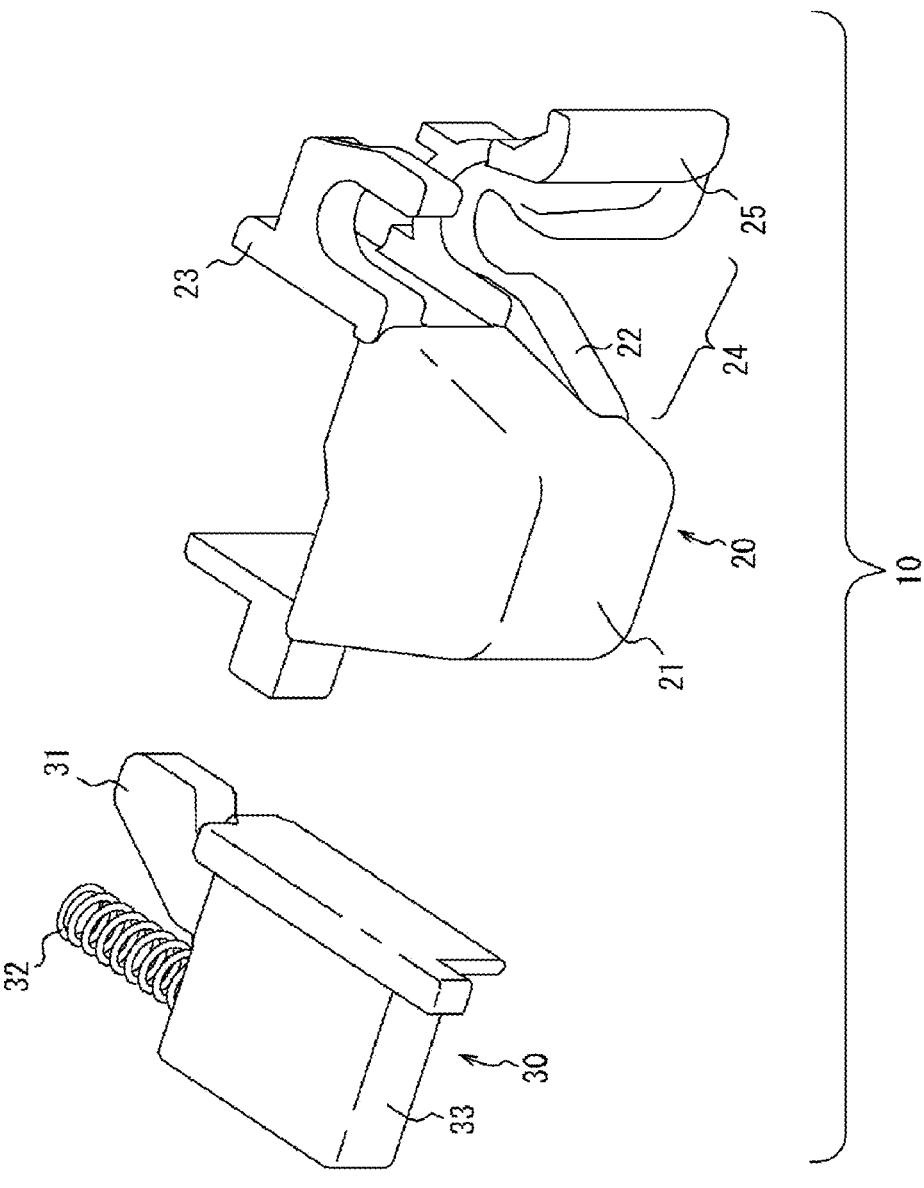

As illustrated in FIGS. 2A and 2B, the mounting portion 7 is configured to be mountable to the first clip member 40 attached to the infusion tube as a liquid feeding tube 46 used for feeding the infusion solution. That is, the mounting portion 7 has a shape conforming to the first clip member 40. More specifically, the mounting portion 7 is configured in a manner that the mounting of the first clip member 40 can be detected by a detection unit 62 described below. Note that, in FIG. 2B, the liquid feeding tube 46 is omitted for convenience of description. This will be described below in detail.

As illustrated in FIGS. 4A, 4B, 4C, 5A, and 5B, the adapter 10 can be attached to the mounting portion 7. The adapter 10 attached to the mounting portion 7 can be mounted to the second clip member 50 attached to a nutrient tube as a liquid feeding tube 55 used for feeding a nutrient. More specifically, the adapter 10 is configured in a manner that the mounting of the second clip member 50 can be detected by the detection unit 62 described below in a state of being attached to the mounting portion 7. In addition, the adapter 10 is configured to enable mounting of the second clip member 50 to the liquid feeding pump 100 but disable mounting of the first clip member 40 to the liquid feeding pump 100. The adapter 10 has a shape that can be attached to the mounting portion 7, and is detachably attached to the mounting portion 7. Therefore, the adapter 10 is removed from the mounting portion 7 when the first clip member 40 is attached, and the adapter 10 is attached to the mounting portion 7 when the second clip member 50 is attached. As described below, in the present embodiment, the adapter 10 includes a cover member 20 and a detection assisting member 30. However, another form of adapter may be used.

As illustrated in FIG. 1, the door portion 110 includes a door housing 103. The door housing 103 is pivotally attached to a housing 12 of the main body portion 120 via a hinge portion 101. In this manner, the door portion 110 of the present embodiment is configured to be openable and closable with respect to the main body portion 120.

On the back surface side of the door portion 110, a door seal rubber 106 is disposed. The door seal rubber 106 is formed of an elastomer, and prevents the medicinal solution from entering the inside of the main body portion 120 in the closed state of the door portion 110.

In addition, a position holding portion 102 is disposed on the back surface side of the door portion 110. When the door portion 110 is closed with respect to the main body portion 120, the position holding portion 102 positions the liquid feeding tubes 55 and 46 by abutting on the liquid feeding tubes 55 and 46.

In addition, the receiving portion 104 is disposed on the back surface side of the door portion 110. The receiving portion 104 sandwiches the liquid feeding tubes 55 and 46 together with the pressing portion 2. In addition, the receiving portion 104 is disposed to face the pressing portion 2. The pressing portion 2 can press the liquid feeding tubes 55 and 46 sandwiched between the pressing portion 2 and the receiving portion 104 toward the receiving portion 104.

Next, a configuration for detecting mounting of the first clip member 40 and the second clip member 50 in the liquid feeding pump 100 will be described. As illustrated in FIG. 2A, the first clip member 40 is mounted to an infusion tube (hereinafter, this is referred to as an "infusion tube 46") as a liquid feeding tube 46 for feeding an infusion solution. As illustrated in FIG. 2B, the first clip member 40 is configured to be insertable into the insertion hole of the mounting portion 7. A detection mechanism 60 is provided when the liquid feeding pump 100 moves from the mounting portion 7 to the inside of the main body portion 120. In the present embodiment, the detection mechanism 60 includes a semicircular columnar rotation unit 61 and the detection unit 62, but a detection mechanism of another form may be used. The illustrated infusion tube 46 and the first clip member 40 constitute a liquid feeding set.

Referring to FIG. 2B, when the first clip member 40 is attached to the mounting portion 7, a protruding distal end portion 41 of the first clip member 40 collides with the radial rotation unit 61 of the detection mechanism 60. By the collision, the semicircular columnar rotation unit 61 rotates about a central axis positioned at a substantially circular central portion of the semicircular bottom surface. When the rotation unit 61 rotates, the position of the concave portion formed on the curved side surface on the arc of the rotation unit 61 coincides with the position of the detection unit 62. As a result, the detection unit 62 of the detection mechanism 60 detects the first clip member 40. Accordingly, the liquid feeding pump 100 can detect that the first clip member 40 is mounted to the mounting portion 7.

As described above, FIG. 3 illustrates the adapter 10 that can be attached to the mounting portion 7 of the liquid feeding pump 100 and the second clip member 50 that can be attached to the mounting portion 7 via the adapter 10. In the present embodiment, the adapter 10 includes the cover member 20 and the detection assisting member 30. However, the form of the adapter 10 is not limited to the present embodiment.

The cover member 20 includes a first portion 21, a second portion 25, an upstream tube fixing portion 23, and a downstream tube fixing portion 22. Hereinafter, for convenience of description, in a front view of the main body portion 120 in a state in which the cover member 20 is attached to the mounting portion 7, the first portion 21 positioned on the left side of an insertion space 24 described below will be referred to as a "left portion 21," and the second portion 25 positioned on the right side of the insertion space 24 will be referred to as a "right portion 25." The left portion 21, the right portion 25, the upstream tube fixing portion 23, and the downstream tube fixing portion 22 define the insertion space 24 that enables insertion of the second clip member 50 but does not disable insertion of the first clip member 40. The upstream tube fixing portion 23 and the downstream tube fixing portion 22 include a concave portion for fixing a nutrient tube (hereinafter, this is referred to as a "nutrient tube 55") as the liquid feeding tube 55 to which the second clip member 50 is attached. In the cover member 20 of the present embodiment, the concave portion of the upstream tube fixing portion 23 and the concave portion of the downstream tube fixing portion 22 are aligned in a manner that the nutrient tube 55 extends substantially vertically in a state of being attached to the mounting portion 7 of the liquid feeding pump 100. In addition, the cover member 20 can be fixed to the main body portion 120 by fixing the left side surface of the left portion 21 and the right side surface of the right portion 25 to the vicinity of the inlet of the insertion hole of the mounting portion 7.

The detection assisting member 30 includes a distal end portion 31, an elastic portion 32, and a member main body portion 33. The distal end portion 31 protrudes from the distal end surface of the member main body portion 33. In addition, the elastic portion 32 is disposed adjacent to the distal end portion 31, extends from the distal end surface of the member main body portion 33 in the same direction as the protruding direction of the distal end portion 31, and is configured to be elastically deformable in this direction. The elastic portion 32 is formed of, for example, a coil spring. The elastic portion 32 is attached to the mounting portion 7 of the liquid feeding pump 100 to be sandwiched between the distal end surface of the member main body portion 33 and a reaction force wall portion 63 of the main body portion 120 of the liquid feeding pump 100 (see FIG. 4B). The detection assisting member 30 enables the detection unit 62 of the detection mechanism 60 to detect the second clip member 50. More specifically, the adapter 10 is attached to the mounting portion 7 in the order of the detection assisting member 30 and the cover member 20, and the second clip member 50 is inserted into the insertion space 24 defined by the cover member 20. As a result, the member main body portion 33 of the detection assisting member 30 is pressed by the second clip member 50. As a result, the elastic portion 32 is compressed and deformed between the member main body portion 33 and the reaction force wall portion 63.

The distal end portion 31 protruding from the member main body portion 33 moves toward the side of the detection unit 62 through the opening adjacent to the reaction force wall portion 63 and extending toward the detection unit 62, and collides with the rotation unit 61 of the detection mechanism 60 provided at the depth of the insertion hole of the mounting portion 7. When the distal end portion 31 collides with the rotation unit 61, the rotation unit 61 rotates, and the position of the concave portion formed on the curved side surface on the arc of the rotation unit 61 coincides with the position of the detection unit 62. As a result, the detection unit 62 detects the second clip member 50. As described above, in the present embodiment, the detection assisting member 30 moves by being pressed by the second clip member 50, realizing the detection of the second clip member 50.

The second clip member 50 includes a rear end portion 51, a clip main body portion 52, and a hook 53. The clip main body portion 52 is provided with an opening 54 through which the nutrient tube 55 penetrates. The hook 53 is configured to engage with the cover member 20 attached to the mounting portion 7.

Figure 4A:
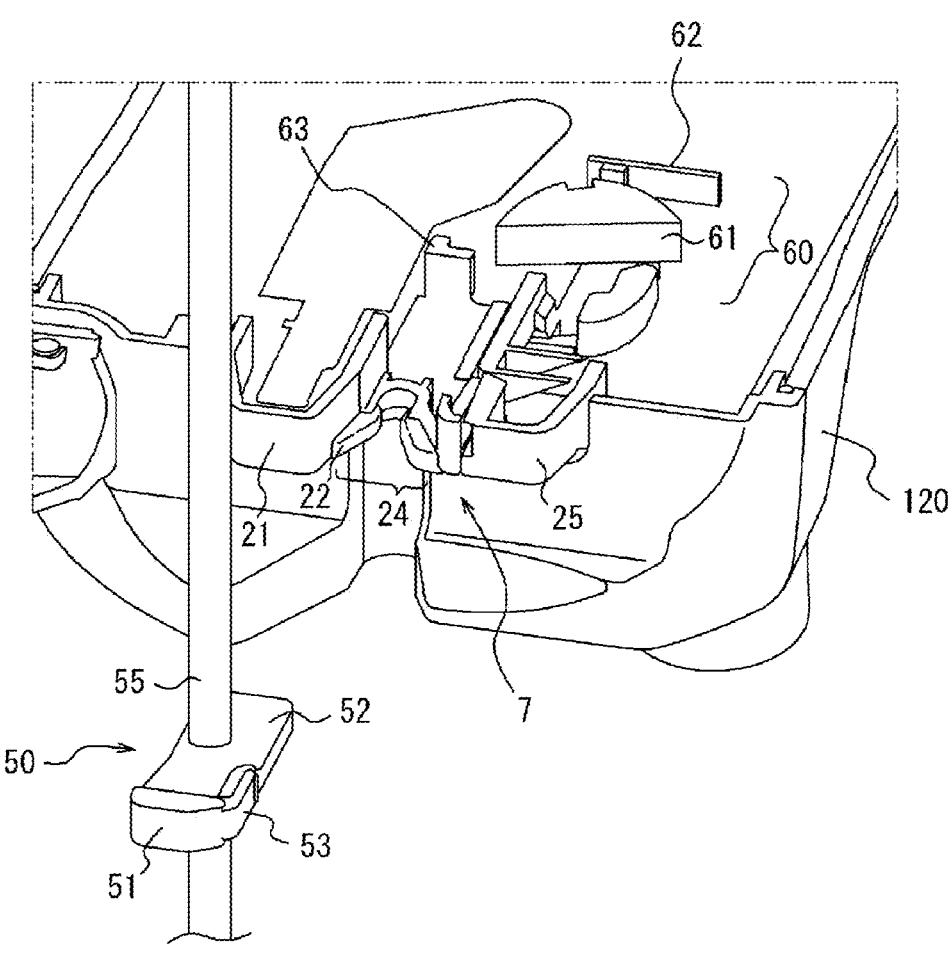
FIG. 4A illustrates a cross-sectional perspective view of the liquid feeding pump taken along line AA' in FIG. 1 in a state in which only a cover member of the adapter illustrated in FIG. 3 is mounted, and the second clip member before being mounted to the adapter.

FIG. 4A illustrates a cross-sectional perspective view of the liquid feeding pump 100 taken along line AA' in FIG. 1 in a state in which only the cover member 20 of the adapter 10 is mounted to the mounting portion 7, and the second clip member 50 mounted to the nutrient tube 55 that feeds nutrients. Originally, the detection assisting member 30 is attached to the mounting portion 7 before the cover member 20 is attached, but FIG. 4A illustrates a state in which only the cover member 20 is attached for convenience of description. Note that the second clip member 50 is previously attached to the illustrated nutrient tube 55, and constitutes a liquid feeding set together with the nutrient tube 55.

Figure 4B:
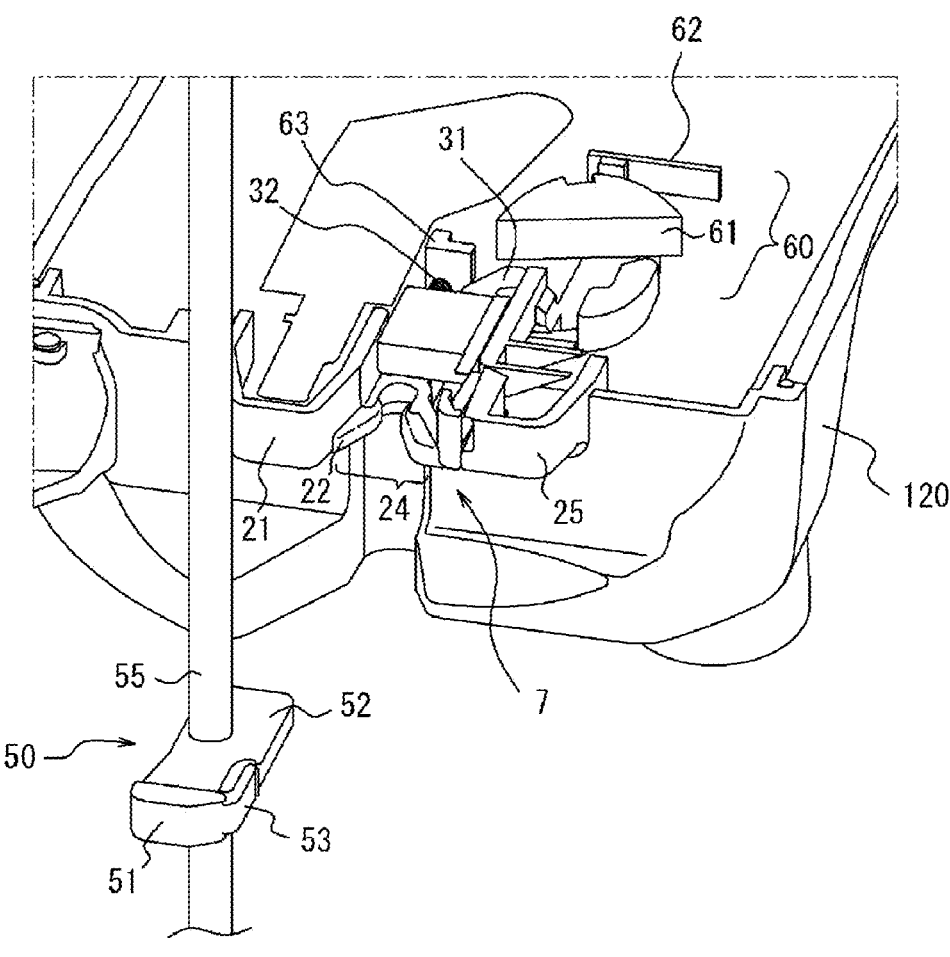
FIG. 4B illustrates a cross-sectional perspective view of the liquid feeding pump taken along line AA' in FIG. 1 in a state in which both the cover member and a detection assisting member constituting the adapter illustrated in FIG. 3 are mounted, and the second clip member before being mounted to the adapter.

FIG. 4B is a cross-sectional perspective view of the liquid feeding pump 100 taken along line AA' in FIG. 1 in a state in which both the cover member 20 and the detection assisting member 30 of the adapter 10 are mounted to the mounting portion 7. As illustrated in FIG. 4B, the elastic portion 32 is installed in a state of being sandwiched between the member main body portion 33 and the reaction force wall portion 63 of the main body portion 120 in the insertion hole of the mounting portion 7. The detection assisting member 30 cannot move further inward due to the elastic force of the elastic portion 32. Therefore, unless the member main body portion 33 is pressed against the elastic force of the elastic portion 32 to approach the rotation unit 61, the distal end portion 31 does not reach the rotation unit 61 of the detection mechanism 60 and does not contact the rotation unit 61.

Figure 4C:
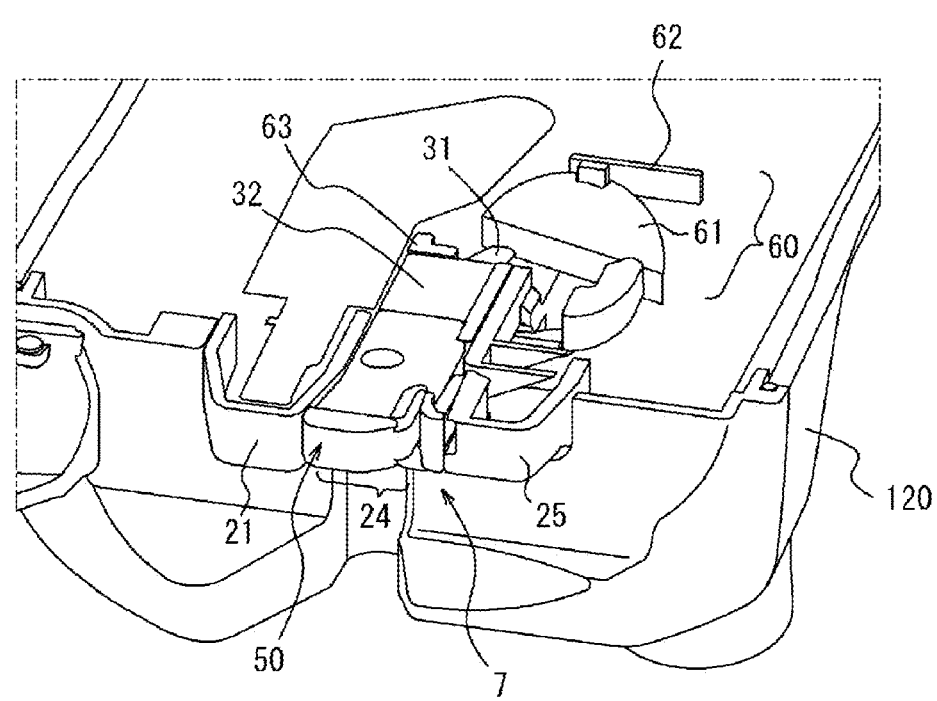
FIG. 4C illustrates a state in which the second clip member is completely mounted to the adapter mounted to the mounting portion of the liquid feeding pump from the state illustrated in FIG. 4B.
Figure 6:
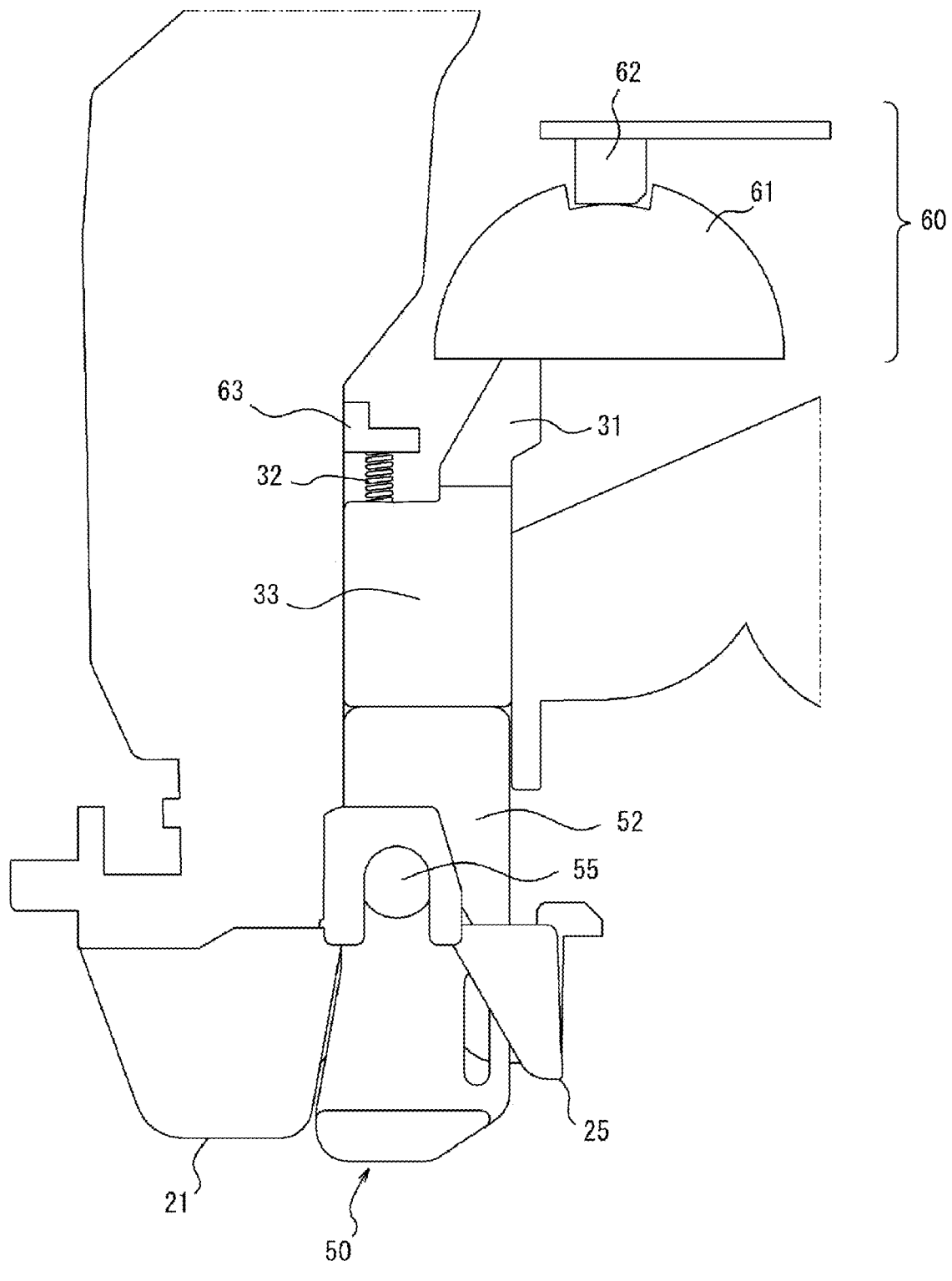
FIG. 6 illustrates a plan view of the mounting portion of the liquid feeding pump and a detection mechanism according to the embodiment of the present application.

FIG. 4C illustrates a state in which the second clip member 50 is inserted into the insertion space 24 of the cover member 20 and the second clip member 50 presses the detection assisting member 30. In addition, FIG. 6 illustrates a plan view of the mounting portion 7 of the liquid feeding pump 100 and the detection mechanism 60. As illustrated in FIGS. 4C and 6, the detection assisting member 30 is pressed by the second clip member 50 to be detected by the detection unit 62. Specifically, the member main body portion 33 of the detection assisting member 30 is pressed by the clip main body portion 52 of the second clip member 50. As a result, the member main body portion 33 moves in a direction approaching the reaction force wall portion 63 against the elastic force of the elastic portion 32. Therefore, the distal end portion 31 disposed adjacent to the elastic portion 32 moves toward the rotation unit 61 of the detection mechanism 60 through the opening adjacent to the reaction force wall portion 63 and presses the rotation unit 61. The rotation unit 61 is rotated by pressing by the distal end portion 31, and the concave portion of the rotation unit 61 moves to the position of the detection unit 62. Accordingly, the detection unit 62 detects that the second clip member 50 is mounted to the mounting portion 7 via the adapter 10. As described above, the liquid feeding pump 100 to which the adapter 10 is attached can detect the mounting of the second clip member 50. In response to the detection mechanism 60 recognizing the second clip member 50, the liquid feeding pump 100 can perform the liquid feeding operation in response to the request of the user. As described above, in the present embodiment, the detection assisting member 30 moves by being pressed by the second clip member 50, realizing the detection of the second clip member 50. As a result, the nutrient can be fed by the liquid feeding pump 100 for infusion.

Figure 5A:
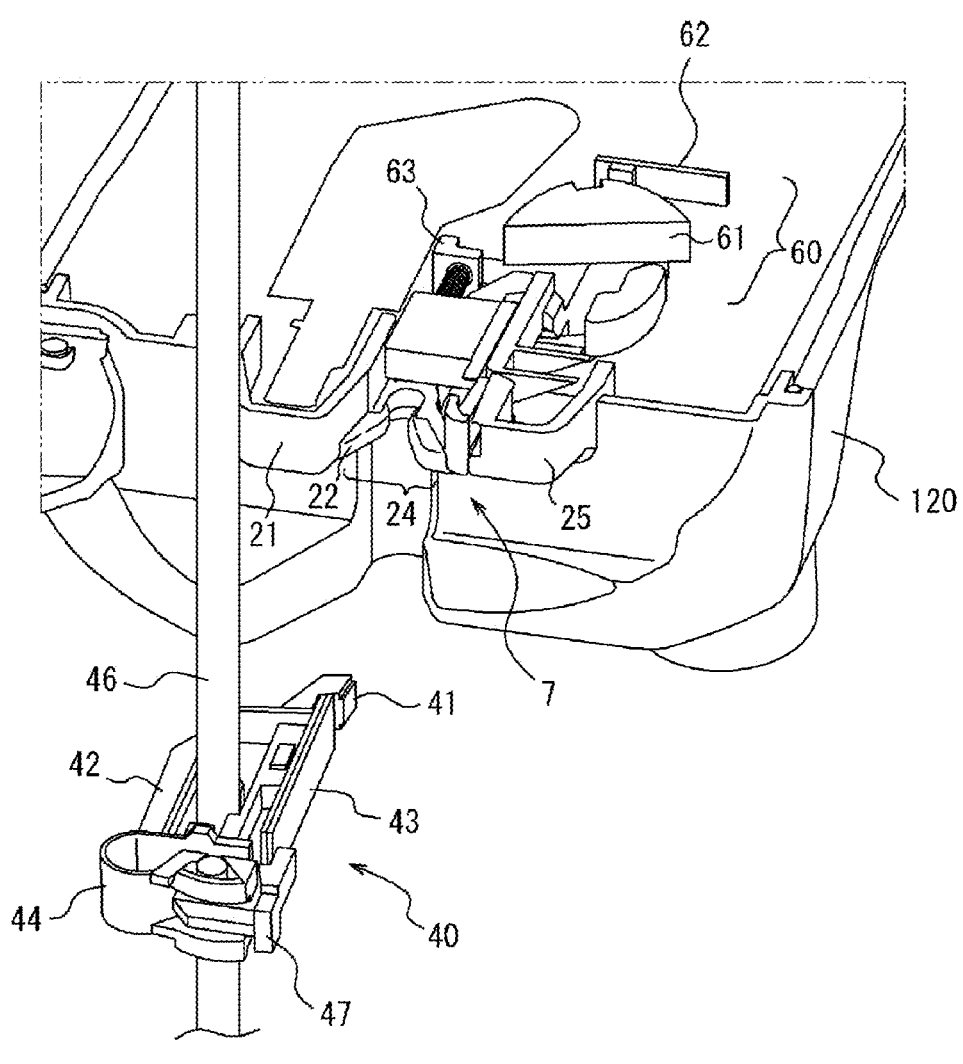
FIG. 5A illustrates a cross-sectional perspective view of the liquid feeding pump taken along line AA' in FIG. 1 in a state in which both the cover member and the detection assisting member constituting the adapter illustrated in FIG. 3 are mounted, and the first clip member.

FIG. 5A illustrates a cross-sectional perspective view of the liquid feeding pump 100 taken along line AA' in FIG. 1 in a state in which both the cover member 20 and the detection assisting member 30 of the adapter 10 is mounted to the mounting portion 7, and the first clip member 40 mounted to the infusion tube 46. Note that the first clip member 40 is previously attached to the illustrated infusion tube 46, and constitutes a liquid feeding set together with the infusion tube 46.

Figure 5B:
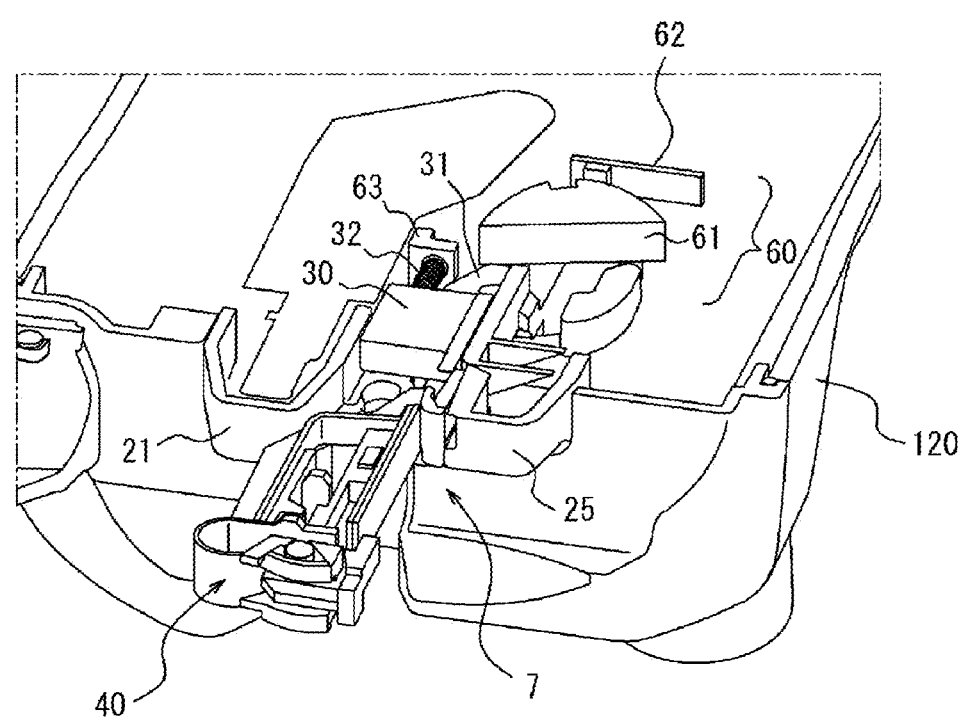
FIG. 5B illustrates that the first clip member cannot be mounted to the adapter in the state illustrated in FIG. 5A.

FIG. 5B illustrates a case in which the first clip member 40 is to be mounted in a state in which both the cover member 20 and the detection assisting member 30 are mounted to the mounting portion 7 of the liquid feeding pump 100. The detection assisting member 30 is not in contact with the first clip member 40 and is not pressed by the first clip member 40, and thus is not detected by the detection unit 62. Specifically, the insertion space 24 defined by the cover member 20 is defined to disable insertion of the first clip member 40. Therefore, the first clip member 40 cannot be inserted into the insertion space 24. Therefore, the first clip member 40 does not come into contact with the detection assisting member 30 positioned at the depth of the insertion space 24, and cannot press the detection assisting member 30. Therefore, the detection assisting member 30 does not move against the elastic force of the elastic portion 32 and does not move to the inside of the main body portion 120. Therefore, the rotation unit 61 is not pressed by the distal end portion 31. Therefore, the detection unit 62 of the detection mechanism 60 cannot detect that the first clip member 40 is mounted to the liquid feeding pump 100. As described above, in the present embodiment, the cover member 20 of the adapter 10 prevents insertion of the first clip member 40, in a manner that the first clip member 40 cannot be mounted to the mounting portion 7.

As described above, the insertion space 24 of the cover member 20 is defined to enable insertion of the second clip member 50 and disable insertion of the first clip member 40. Therefore, in a case in which the cover member 20 is mounted to the mounting portion 7, the first clip member 40 cannot be mounted to the mounting portion 7. As a result, it is possible to prevent the infusion tube 46 from being erroneously mounted when the nutrient tube 55 is to be mounted to the liquid feeding pump 100.

Figure 7:
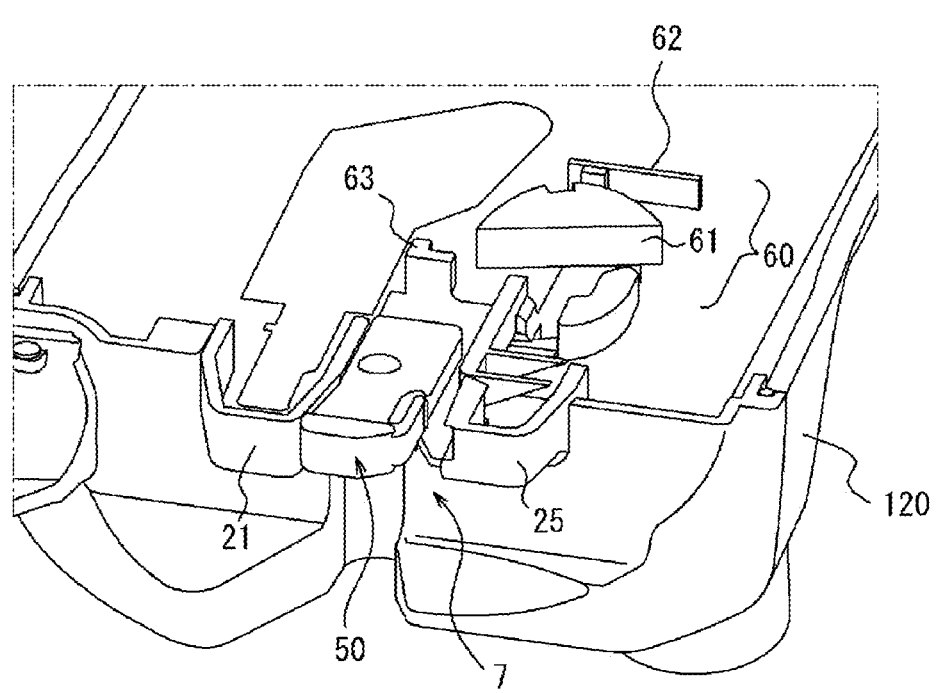
FIG. 7 illustrates a cross-sectional perspective view of the liquid feeding pump taken along line AA' in FIG. 1 in the state in which only the cover member of the adapter illustrated in FIG. 3 is mounted, and the second clip member inserted into an insertion space of the cover member.

FIG. 7 is a cross-sectional perspective view of the liquid feeding pump 100 taken along line AA' in FIG. 1 in a state in which only the cover member 20 of the adapter 10 is attached to the mounting portion 7. FIG. 7 illustrates a state in which the detection assisting member 30 is not disposed in the insertion hole of the mounting portion 7 and only the second clip member 50 is inserted into the insertion space 24 of the cover member 20. The depth of the insertion space 24 (the depth length from the inlet of the insertion hole of the mounting portion 7 of the main body portion 120 to the inside of the main body portion 120) is longer than the length of the second clip member 50. In addition, because the distal end of the second clip member 50 is substantially flat, the second clip member abuts on the reaction force wall portion 63 and cannot press the rotation unit 61 beyond the reaction force wall portion 63. Moreover, because the opening 54 through which the nutrient tube 55 penetrates is provided near the center of the clip main body portion 52 of the second clip member 50, even if only the second clip member 50 is inserted into the insertion space 24, the nutrient tube 55 penetrating the opening 54 of the second clip member 50 abuts on the housing 12 of the main body portion 120, in a manner that the second clip member 50 does not reach the rotation unit 61 and cannot press the rotation unit 61. As described above, the adapter 10 of the present embodiment does not enable the mounting of the second clip member 50 only with the cover member 20, but the adapter 10 is not limited to such a two-component configuration, and may be a one-component configuration, for example. In FIG. 7, the description has been made based on the state in which only the cover member 20 of the adapter 10 is mounted to the mounting portion 7, but the same applies to the state in which the cover member 20 is not mounted to the mounting portion 7.

FIG. 8 illustrates details of the first clip member 40 alone. The first clip member 40 includes the distal end portion 41, a left portion 42, a right portion 43, a first opening and closing portion 44 connected to the left portion 42, and a second opening and closing portion 47 connected to the right portion 43. Here, similarly to the cover member 20 described above, "left and right" means left and right of the main body portion 120 in a front view in a state in which the first clip member 40 is mounted to the mounting portion 7. The distal end portion 41 has the same shape as the distal end portion 31 of the detection assisting member 30. The first clip member 40 is made of a deformable material. The left portion 42, the right portion 43, and the first opening and closing portion 44 define an opening 45. When the first clip member 40 is attached to the infusion tube 46, the infusion tube 46 penetrates through the opening 45. The left portion 42 is displaceable with respect to the right portion 43 to change the size of the opening 45. The first opening and closing portion 44 and the second opening and closing portion 47 can be engaged with each other. In a state of not being pressed from the outside, the left portion 42 is disposed to form a predetermined angle with respect to the right portion 43.

Figure 8A:
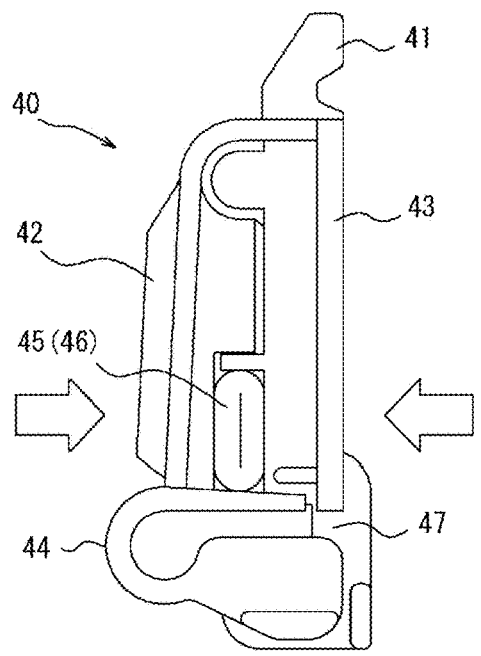
FIG. 8A illustrates one form of the first clip member illustrated in FIG. 2A.

FIG. 8A illustrates a state in which the left portion 42 and the right portion 43 approach each other by being pressed in the direction indicated by the arrow. As a result, the first opening and closing portion 44 connected to the left portion 42 and the second opening and closing portion 47 connected to the right portion 43 are also brought close to and engaged with each other. Accordingly, the opening 45 is narrowed, and the infusion tube 46 in the opening 45 is closed.

Figure 8B:
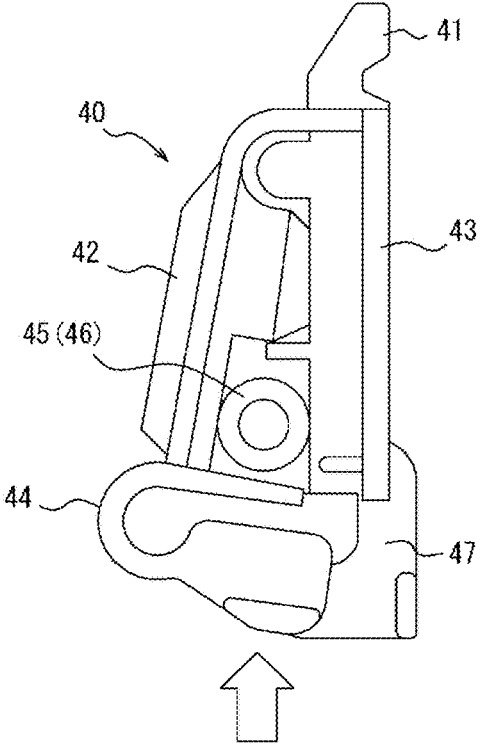
FIG. 8B illustrates another form of the first clip member illustrated in FIG. 2A.

FIG. 8B illustrates a state in which the first opening and closing portion 44 is released from the engagement with the second opening and closing portion 47 by being pressed in the direction of the arrow. As a result, the left portion 42 connected to the first opening and closing portion 44 is displaced to be separated from the right portion 43 connected to the second opening and closing portion 47. Accordingly, the opening 45 expands, and the closing of the infusion tube 46 in the opening 45 is released.

As described above, the mounting portion 7 of the liquid feeding pump 100 is configured to enable mounting of the first clip member 40. The mounting of the first clip member 40 is completed when the first clip member 40 is pushed into the insertion hole of the mounting portion 7 of the main body portion 120 and the distal end portion 41 of the first clip member 40 is detected by the detection unit 62. The first clip member 40 is mounted to the mounting portion 7 of the main body portion 120 in a state in which the door portion 110 is open with respect to the main body portion 120. At this time, the first clip member 40 is mounted to the mounting portion 7 in the state illustrated in FIG. 8A, and this state is maintained. Specifically, a force is received from both sides of the mounting portion 7 in the direction of the arrow in FIG. 8A. As a result, the left portion 42 and the right portion 43 of the first clip member 40 receive a force approaching each other. Because the left portion 42 is connected to the first opening and closing portion 44 and the right portion 43 is connected to the second opening and closing portion 47, the first opening and closing portion 44 and the second opening and closing portion 47 also approach each other when the left portion 42 and the right portion 43 receive a force to approach each other. As a result, the first opening and closing portion 44 and the second opening and closing portion 47 are engaged with each other. Therefore, the infusion tube 46 in the opening 45 is closed. This prevents an unintended flow of the infusion due to forgetting to close the clamp.

After the first clip member 40 is mounted to the mounting portion 7, the first clip member 40 is sandwiched between the main body portion 120 and the door portion 110. Accordingly, the first clip member 40 receives a force in the direction of the arrow in FIG. 8B by the door portion 110. As a result, the engagement between the first opening and closing portion 44 and the second opening and closing portion 47 is released, and the left portion 42 is displaced to be separated from the right portion 43. As a result, the closing of the infusion tube 46 is released.

REFERENCE SIGNS LIST

Reference Character List

1 Air bubble detection sensor
2 Pressing portion
3 Finger
4 Tube position defining unit
5 Closing sensor unit
6 Handle
7 Mounting portion
8 Ultrasonic transmission unit
9 Ultrasonic reception unit
10 Adapter
12 Housing
20 Cover member
21 First portion (left portion)
22 Downstream tube fixing portion
23 Upstream tube fixing portion
24 Insertion space
25 Second portion (right portion)
30 Detection assisting member
31 Distal end portion
32 Elastic portion
33 Member main body portion
40 First clip member
41 Distal end portion
42 Left portion
43 Right portion
44 First opening and closing portion
45 Opening
46 Liquid feeding tube (infusion tube)
47 Second opening and closing portion
50 Second clip member
51 Rear end portion
52 Clip main body portion
53 Hook
54 Opening
55 Liquid feeding tube (nutrient tube)
60 Detection mechanism
61 Rotation unit
62 Detection unit
63 Reaction force wall portion
101 Hinge portion
102 Position holding portion
103 Door housing
104 Receiving portion
106 Door seal rubber
110 Door portion
120 Main body portion

The invention claimed is:

1. A liquid feeding pump for feeding liquid in a liquid feeding tube, the liquid feeding pump comprising:

a mounting portion to which a first clip member mounted to the liquid feeding tube is mountable;

an adapter detachably attachable to the mounting portion; and a detection unit configured to detect mounting of the first clip member to the mounting portion, wherein:

the adapter has a shape that disables detection by the detection unit of mounting of the first clip member by the detection unit and enables detection by the detection unit of mounting of a second clip member having a shape different from a shape of the first clip member.

2. The liquid feeding pump according to claim 1, wherein:

the adapter defines an insertion space formed to disable insertion of the first clip member and enable insertion of the second clip member.

3. The liquid feeding pump according to claim 2, wherein:

the adapter comprises:

a cover member that defines the insertion space, and a detection assisting member that is detected by the detection unit by being pressed and moved or deformed by the second clip member inserted into the insertion space.

4. A system comprising:

the liquid feeding pump according to claim 1; and the liquid feeding tube, which is an infusion tube configured to feed an infusion solution; wherein:

the first clip member is mounted to the infusion tube.

5. A system comprising:

the liquid feeding pump according to claim 1; and a nutrient tube configured to feed a nutrient; wherein:

the second clip member is mounted to the nutrient tube.

6. The liquid feeding pump according to claim 1, comprising:

a main body portion configured to control feeding of the liquid; and a door portion pivotably connected to the main body portion; wherein:

the door portion and the main body portion are configured to sandwich the liquid feeding tube when the door portion is closed with respect to the main body portion; and when the first clip member is mounted to the mounting portion in a state in which the door portion is open with respect to the main body portion, the mounting portion is configured to close the liquid feeding tube to which the first clip member is mounted.

7. The liquid feeding pump according to claim 6, wherein:

the mounting portion is configured such that, after the first clip member is mounted to the mounting portion and the door portion is closed with respect to the main body portion, closing of the liquid feeding tube is released.

8. An adapter for use with a liquid feeding pump, the liquid feeding pump comprising a mounting portion to which a first clip member mounted to a liquid feeding tube is mountable, and a detection unit that detects mounting of the first clip member to the mounting portion, the adapter having:

a shape that disables detection of mounting of the first clip member by the detection unit and enables detection of mounting of a second clip member having a shape different from a shape of the first clip member by the detection unit, wherein:

the adapter is configured to be detachably attached to the mounting portion.

9. The adapter according to claim 8, wherein the adapter defines an insertion space formed to disable insertion of the first clip member and enable insertion of the second clip member.

10. The adapter according to claim 9, comprising:

a cover member that defines the insertion space; and a detection assisting member that is detected by the detection unit by being pressed and moved or deformed by the second clip member inserted into the insertion space.

11. A liquid feeding set for use in a liquid feeding pump, the liquid feeding set comprising:

a liquid feeding tube; and a clip member attached to the liquid feeding tube, the clip member comprising a hook configured to engage with a cover member of an adapter, wherein:

the clip member has a shape that cannot be mounted to a mounting portion of the liquid feeding pump and can be mounted to the liquid feeding pump only via the adapter attached to the mounting portion.

* * * * *